(12) United States Patent
Puckett, Jr. et al.

(10) Patent No.: US 7,259,210 B2
(45) Date of Patent: Aug. 21, 2007

(54) BONE CEMENT AND A SYSTEM FOR MIXING AND DELIVERY THEREOF

(75) Inventors: Aaron D. Puckett, Jr., Madison, MS (US); Jack Lemons, Birmingham, AL (US); Lujia Bu, Shrewsbury, MA (US); Jimmy W. Mays, Knoxville, TN (US)

(73) Assignee: The UAB Research Foundation, Birmingham, AL (US)

( * ) Notice: Subject to any disclaimer, the term of this patent is extended or adjusted under 35 U.S.C. 154(b) by 92 days.

(21) Appl. No.: 10/470,480

(22) PCT Filed: Jan. 28, 2002

(86) PCT No.: PCT/US02/03923

§ 371 (c)(1),
(2), (4) Date: Jan. 27, 2004

(87) PCT Pub. No.: WO02/058592

PCT Pub. Date: Aug. 1, 2002

(65) Prior Publication Data

US 2004/0132859 A1 Jul. 8, 2004

Related U.S. Application Data

(60) Provisional application No. 60/264,440, filed on Jan. 26, 2001.

(51) Int. Cl.
| | |
|---|---|
| *C08F 8/00* | (2006.01) |
| *C08L 37/00* | (2006.01) |
| *C08L 41/00* | (2006.01) |
| *C08L 9/00* | (2006.01) |
| *C08L 23/04* | (2006.01) |
| *A61F 2/28* | (2006.01) |
| *A61F 2/00* | (2006.01) |

(52) U.S. Cl. ............... 525/193; 525/208; 525/232; 525/240; 525/241; 623/23.62; 523/115; 523/116

(58) Field of Classification Search ............... 525/191, 525/193, 208, 232, 240, 241; 623/23.62; 523/115, 116
See application file for complete search history.

(56) References Cited

U.S. PATENT DOCUMENTS

| | | | |
|---|---|---|---|
| 4,338,925 A | 7/1982 | Miller | |
| 4,341,691 A | 7/1982 | Anuta | |
| 4,515,930 A * | 5/1985 | Omura et al. | ............... 526/276 |
| 4,554,686 A * | 11/1985 | Baker | ............... 606/92 |
| 5,084,491 A * | 1/1992 | Kerby | ............... 523/116 |
| 5,106,614 A | 4/1992 | Posey-Dowty et al. | |
| 5,155,252 A * | 10/1992 | Yamamoto et al. | ............ 560/190 |
| 5,334,626 A | 8/1994 | Lin | |
| 5,336,699 A | 8/1994 | Cooke et al. | |
| 6,086,594 A | 7/2000 | Brown | |
| 6,689,823 B1 * | 2/2004 | Bellare et al. | ............... 523/115 |

* cited by examiner

*Primary Examiner*—Nathan M. Nutter
(74) *Attorney, Agent, or Firm*—Gifford, Krass, Sprinkle, Anderson & Citkowski PC

(57) ABSTRACT

A bone cement formulation stored as a solid component pack having 0.3 to 20 solid component pack weight percent of an elastomer and a polymer bead core having a polyacrylate terminated surface. The second component pack is a liquid component pack including an acrylate monomer. An alternate solid component pack includes 3 to 25 solid component pack weight percent of a polyacrylate and a rubber toughened polymethyl methacrylate. A cement mixing and delivering system according to the present invention includes a tube having an exit nozzle and an aperture. An end plate is adapted to seal against the interior of the tube aperture and the end plate has a plurality of needles protruding therefrom into the tube. A rotatable and slidable divider is received within the tube intermediate between the end plate and the exit nozzle. The divider includes at least two plates. Each of the plates has a plurality of apertures that upon alignment the needles of the first plate are urged through the apertures of the at least two divider plates.

10 Claims, 8 Drawing Sheets

Plate 2
Before

Plate 2
After

BONE CEMENT AND A SYSTEM FOR MIXING AND DELIVERY THEREOF

FIELD OF THE INVENTION

The present invention relates generally to orthopedic adhesives and, more particularly, to rubber toughened bone cement formulations.

BACKGROUND OF THE INVENTION

A milestone achievement in the bone cement surgery was Charnley's development of polymethyl methacrylate (PMMA) bone cement used for artificial joint fixation in 1959. Almost forty years later, PMMA remains the standard material for anchoring total joint implants to the skeleton. During this time, there have been numerous improvements in prosthesis design and implantation techniques to improve the clinical, restorative and rehabilitative aspects of the total hip arthroplasties. The success rate of cemented hip arthroplasties at 10 years exceeds 90% in patients aged 60 years or more when proper cementing techniques are used. However, despite the improvements, PMMA has several recognized shortcomings as a structural material. Aseptic loosening remains the major long-term problem with total joint replacement.

In a bone cement system, there are three different materials (bone, cement, and implant) and two interfaces (bone and bone cement, bone cement and implant). The properties at the interfaces are mismatched because the cement is much weaker than the bone and the implant. Fatigue and fracture of cement were implicated in the failure of these devices. Loosened prostheses, as defined by Harris et al. generally require revision surgery. The total cost of a primary total hip arthroplasty is substantial. The cost of revision surgery may be even greater. The life expectancy of a revised prosthesis is considerably lower than that of a primary prosthesis; furthermore, the trauma and pain associated with the primary prosthesis failure, and the revision operation, are taxing on the patient. The reduction of the failure rate in joint arthroplasty, therefore, is a primary goal of biomechanics and biomaterials research.

Classic bone cements are bi-component materials, which are composed of MMA, PMMA, initiators and filler. The solid material forms a plastic paste upon mixing with the liquid phase, usually under vacuum, with a specially designed apparatus. This viscous paste is then transferred into the human body between the prosthesis and bone using a cement delivery system. During this time, the paste solidifies, increasing its mechanical strength progressively up to saturation.

Ever since the introduction of surgical bone cements, there have been many efforts to improve their mechanical properties. Steps to improve the strengths of bone cement have been categorized into various distinctly divergent paths. Addition of reinforcing fiber, designing of new mixing and delivery methods, modifying the powder or liquid components, bioactive cements, and even cementless technology are major fields of focus. Even though there have been some remarkable improvements in bone cement technologies for clinical application, however, not all efforts to produce superior quality bone cement for total joint replacement have so far been successful.

Efforts to improve bone cement properties have been extensive. These efforts largely have involved modification of monomer components and cross linkers. Pascual et al. replaced up to 20%, of the monomer methylmethacrylate (MMA) with the same amount of ethoxytriethylene glycol monomethacrylate (TEG). They found that the addition of this new monomer decreased noticeably the maximum temperature and increased both setting and working times. Mechanical testing revealed that the introduction of TEG gave rise to a less fragile bone cement by increasing slightly the total deformation without any change in the rest of the tensile parameters.

Crosslinking agents, usually bifunctional dimethacrylates, were used to try to improve the mechanical properties of the acrylic bone cements. At low concentrations of crosslinking agents, the mechanical properties were superior but steadily decreased with increasing concentration. Poly (ethyleneglycol dimethacrylate), EGDMA(400), even when used at very low concentrations, produced a steady improvement in the mechanical properties and could be used in cement formulations with a view to reducing creep and improving mechanical properties.

The same strategy has been applied to PEMA bone cement. Incorporation of triethylene glycol dimethacrylate produced an increase in the tensile strength and modulus with a decrease in the strain at maximum stress. However, polyethylene glycol dimethacrylate (n=400) did not improve the mechanical properties appreciably.

4-methacryloyloxyethyl trimellitate anhydride (4-META) has been added to monomer component as an adhesion promoting agent. Implantation of the 4-META cement in animals demonstrated that these cements did not disturb bone ingrowth and the new bone was able to contact the cement directly. A methacrylic monomer derived from salicylic acid, 5-hydroxy-2-methacrylamidobenzoic acid (5-HMA), was incorporated with 2-hydroxyethyl methacrylate, (HEMA), in different proportions to the liquid phase of acrylic bone cement formulations. 5-HMA monomer shows the ability to form molecular complexes with calcium atoms in order to improve osteointegration in the application of bone cement formulations. Lower peak temperature values were observed when 5-HMA was incorporated with respect to PMMA bone cement.

Hydroxypropyl methacrylate (HPMA) was also one of the candidates to modify bone cements. However, the adhesion properties were unsatisfactory. The problem was solved by increasing the monomer to polymer ratio from 1:2 to 1:1.86.

Radiopaque iodine-containing methacrylate, 2,5-diiodo-8-quinolyl methacrylate and 5,7-diiodo-8-quinolyl methacrylate have been used in the preparation of acrylic radiopaque cements.] The addition of 5 wt % of the iodine-containing methacrylate provided a significant increase in the tensile strength, fracture toughness and ductility, with respect to the barium sulfate-containing cement, since no organic/inorganic interface exist in this system.

Polybutyl methacrylate (PBMA) and polyethyl methacrylate (PEMA) have been used to replace PMMA. Butyl methacrylate monomer was believed to be slightly less toxic than methyl methacrylate monomer. The surface appearance of the broken cement from the two materials differed significantly, showing a series of elevations resembling tightly packed spheres in the case of PMMA, but a smooth surface with only occasional smooth elevations in the case of PEMBMA. PBMA and PEMA modified bone cement also show less bone necrosis and a thinner fibrous tissue layer adjacent to the cement when it is cured intraosseously.

Bone cement formulated from polybutyl methacrylate in a methacrylate matrix (PBMMA) can reduce the modulus of the materials. However, it has much greater long-term subsidence of the implant system.

Although polyethyl methacrylate (PEMA) offers a promising alternative to PMMA due to its high ductility, low toxicity and low exotherm, the fatigue test revealed that specimens made of PEMA was inferior to the that of PMMA in term of the number of cyclic loadings to failure. If HA is fabricated and mixed with PEMA, it can potentially result in an increase in fracture toughness, fatigue crack propagation resistance, and creep resistance, without a decrease in adhesive strength, with decrease in toxicity of acrylic cements, however, the cycles to failure were decreased. When HA particles are treated with a silane-coupling agent, the fatigue strength is enhanced as well.

Traditionally, poly(methyl methacrylate-co-styrene) was synthesized by suspension polymerization. The powder is then mixed with barium sulfate and benzoyl peroxide. The proper formulation of the powder package is still under observation. Synthesis of copolymers of methyl methacrylate-styrene with suitable compounds, particle size distribution, molecular weight and molecular weight distribution for bone cement application have been discussed by Cordovi et al.

Self-reinforced composite poly(methyl methacrylate) (SRC-PMMA) was developed by Wright et al. to use as a pre-coat for hip prostheses or other stemmed prostheses. This material has a similar chemical composition to bone cement, with the matrix and reinforcing fibers both fabricated from PMMA.

The elastomeric copolymer acrylonitrile-butadiene-styrene (ABS) was found to be an excellent material to enhance the mechanical properties of acrylic bone cement. Although strength and stiffness decreased with an increasing second phase volume fraction, ductility and toughness both increased. The crack propagation became stable for specimens containing over a 5% volume fraction of the second phase. The fracture toughness increased up to 60% when the amount of ABS reached 20%. Fatigue crack propagation rate decreased by about 2 orders of magnitude. Size of PMMA Beads PMMA beads for bone cement application generally are made by emulsion polymerization. Ginebra et al. concluded that the use of relatively larger diameter PMMA beads improves the characteristic parameters of the curing process, without detrimental effects on the mechanical properties of the cured cement. Pascual et al. revealed that changing the size distribution of the PMMA beads significantly changes the curing parameters (peak temperature and setting time) of the cement formulations in comparison with the classical behavior of the commercial systems, CMW and ROSTAL, without any noticeable loss in the mechanical properties, such as tensile strength, elastic moduli, compressive strength and plastic strain.

Solutions of PMMA powder predissolved in MMA have been developed as an alternative to current powder/liquid bone cements. They utilized the same addition polymerization chemistry as commercial cements, but in mixing and delivering via a closed system, porosity is eliminated and the dependence of material properties on the surgical technique is decreased. The system is composed of two separate packages with two solutions of constant polymer-to-monomer ratio, but one having BPO initiator and the other having NNDMPT activator. The mechanical properties could be superior to traditional bone cements. We found that the shelf life is not promising for this approach.

For example, the potential advantage of increasing the mechanical strength of bone cement by adding fibers is offset by the increase in the viscosity of the cement. Cementless technology is inapplicable to aged people since bone ingrowth can be difficult to achieve. Even the efforts to reduce the porosity of surgical bone cement were not effectively linked to the long-term outcomes of total hip arthroplasty. On the other hand, there is evidence that bone cement fracture does lead to a certain percentage of prosthesis failure. Therefore, in theory, an improvement in the resistance of the cement material to fracture might also be pivotal to perfecting the overall performance of cemented prosthesis. Thus, there exists a need for a bone cement with overall superior handling and mechanical properties.

The cement typically is provided in two components, powder and liquid monomer. The physician mixes the two shortly before use to form a pourable liquid, which is loaded into a syringe made for the purpose. The liquid rapidly thickens into a viscous paste, requiring considerable force for ejection from the syringe. The syringe is put into a hand-held injector, whereby the viscous paste can be forced out of the syringe into the bone as detailed in U.S. Pat. No. 4,405,249.

During the operation of mixing the cement components and filling the syringe, bubbles of air are inevitably entrained in the liquid; when the liquid thickens, the bubbles cannot escape from the paste. The bubbles of air are expressed with the cement into the bone; and when the cement hardens, the bubbles leave voids in the solidified cement. Thus, there exists a need for a cement delivery system that facilitates rapid mixing and limits bubble entrainment.

SUMMARY OF THE INVENTION

A bone cement formulation includes a solid component pack having 3 to 25 solid weight component pack weight percent of a polyacrylate, and a rubber toughened polymethyl methacrylate. The bone cement formulation also includes a liquid component pack including an acrylate monomer. An alternate cement formulation includes a solid component pack containing 0.3 to 20 solid component pack weight percent of an elastomer and a polymer bead core having a polyacrylate terminated surface. This cement formulation also includes a liquid component pack including an acrylate monomer. The method for securing a prosthetic implant to a bone is detailed which includes applying an inventive bone cement formulation to the prosthesis attachment site and bringing the prosthetic implant into contact with the inventive bone cement. A cement mixing and delivering system according to the present invention includes a tube having an exit nozzle and an aperture. An end plate is adapted to seal against the interior of the tube aperture and the end plate has a plurality of needles protruding therefrom into the tube. A rotatable and slidable divider is received within the tube intermediate between the end plate and the exit nozzle. The divider includes at least two plates. Each of the plates has a plurality of apertures that upon alignment the needles of the first plate are urged through the apertures of the at least two divider plates.

DETAILED DESCRIPTION OF THE INVENTION

Figure 1:
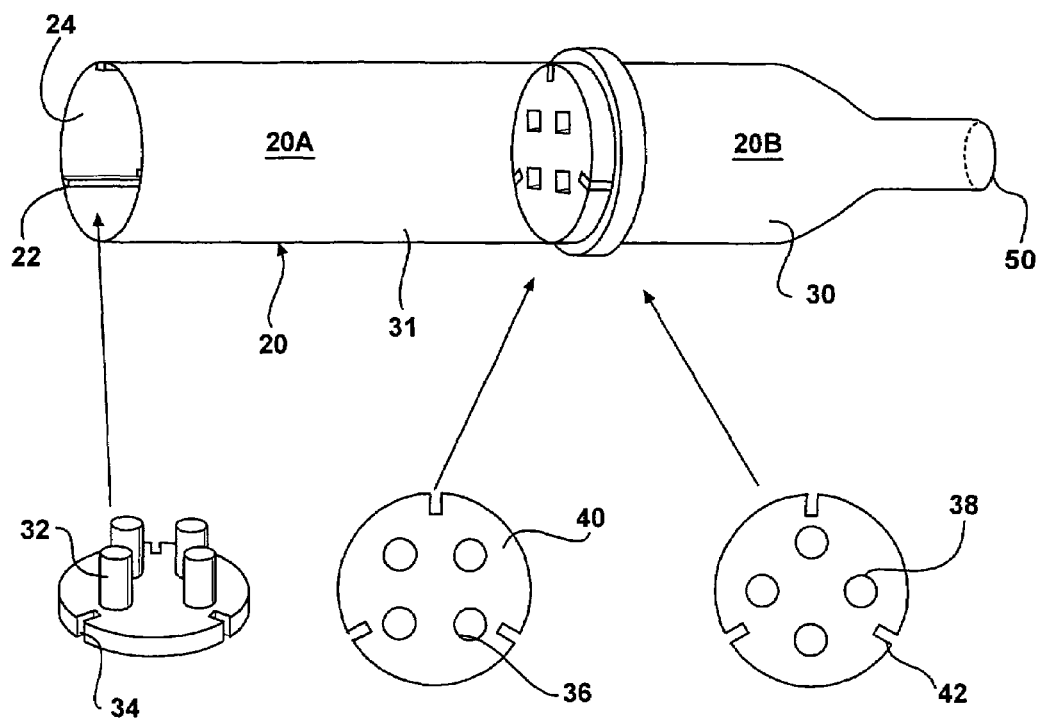
FIG. 1 is a perspective view of an inventive cement mixing and delivery system having two compartments divided by two plates.
Figure 2:
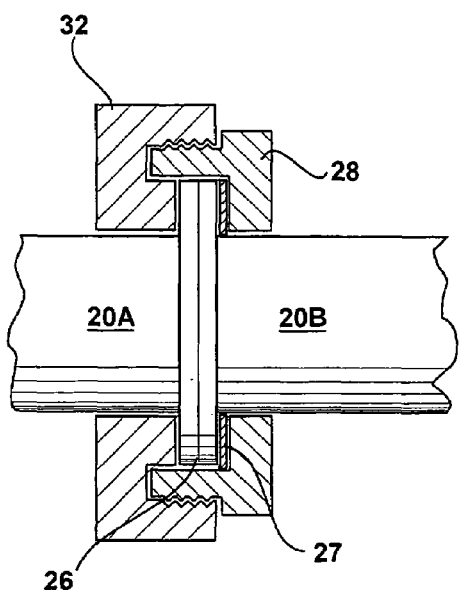
FIG. 2 is a schematic illustration of the connection between storage tube portions.
Figure 3:
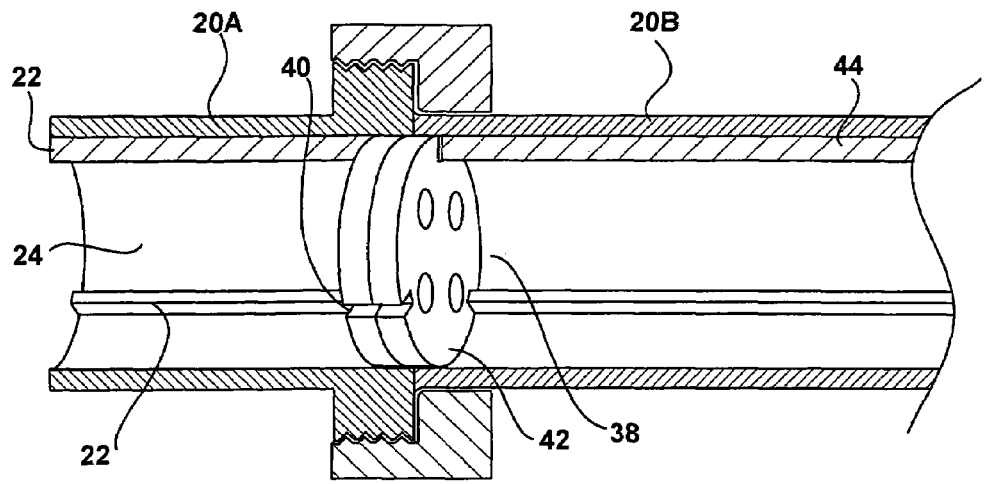
FIG. 3 is a partial cutaway view of the inventive cement mixing and delivery system of FIG. 1.

The cement formulations of the present invention have utility as high mechanical strength bonding materials particularly in the area of bone replacement, bone stabilization, and prosthesis securement. The inventive formulations meet the mechanical property requirements of ASTM F451 while providing ease of mix, low viscosity during handling, and quick setup after injection. An inventive formulation of a polyacrylate containing an elastomeric rubber portion surprisingly acts to improve the handling properties and/or mechanical properties relative to conventional cements.

An inventive formulation is based on a polyacrylate, a polymerizable acrylate monomer and an elastomeric rubber toughener. While the polyacrylate and polymerizable acrylate monomer are admixed from a solid component pack and liquid component pack, respectively, it is appreciated that the elastomeric rubber toughener is provided in either solid or liquid pack depending on such properties as liquid phase solubility, molecular weight, and reactivity toward said polymerizable acrylate monomer.

As used herein, the term "polyacrylate" is defined to include all polymers and copolymers of acrylic acid and acrylic acid esters that are suitable for bone cements that include an acrylate monomer listed hereinbelow. Preferably, the ester is derived from an aliphatic $C_1$-$C_6$ alcohol. More preferably, the ester is the methyl ester.

A polymerizable acrylate monomer as used herein is defined to include a methacrylate or acrylate monomer having at least one unsaturated double bond. A polymerizable acrylate monomer according to the present invention illustratively includes methyl methacrylate, ethyl methacrylate, isopropyl methacrylate, 2-hydroxyethyl methacrylate, n-butyl methacrylate, isobutyl methacrylate, 3-hydroxypropyl methacrylate, tetrahydrofurfuryl methacrylate, glycidyl methacrylate, 2-methoxyethyl methacrylate, 2-ethylhexyl methacrylate, benzyl methacrylate, 2,2-bis(methacryloxyphenyl)propane, 2,2-bis[4-(2-hydroxy-3-methacryloxypropoxy)phenyl]propane, 2,2-bis(4-methacryloxypolyethoxylphenyl)propane, ethylene glycol dimethacrylate, diethylene glycol dimethacrylate, triethylene glycol dimethacrylate, butylene glycol dimethacrylate, neopentyl glycol dimethacrylate, 1,3-butanediol dimethacrylate, 1,4-butanediol dimethacrylate, 1,6-hexanediol dimethacrylate, trimethylolpropane trimethacrylate, trimethylolethane trimethacrylate, pentaerythritol trimethacrylate, trimethylolmethane trimethacrylate and pentaerythritol tetramethacrylate, and methacrylates and acrylates having urethane bonds therein. Specific urethane including acrylates include di-2methacryloxyethyl-2,2,4-trimethylhexamethylene dicarbomate and its acrylate. It is appreciated that phenyl ring containing acrylates are also operative herein.

An elastomeric rubber toughener according to the present invention illustratively includes polyethylene, polypropylene, polybutene, polypentene, ethylene-propylene copolymers, isoprene-butene copolymers, ethylene-butene copolymers, polybutadiene, polyisoprene, hydrogenated polybutadiene, hydrogenated polyisoprene, ethylene-propylene-diene copolymers, ethylene-butene-diene copolymers, butyl rubber, polystyrene, styrene-butadiene copolymers, styrene-hydrogenated butadiene copolymers, and ligand forms thereof at 20° C.

A polymer bead core according to the present invention is defined to include a polymer or copolymer mass having a linear domain dimension of from 0.1 microns to 500 microns and forming a stable interface with a polyacrylate overcoat. A polymer bead core illustratively includes acrylics, acrylates, styrenes, butadienes, alkylenes, carbonates, adipic acids, nylons, vinyl chlorides, urethanes, and isocyanates, and copolymers thereof, especially with acrylates. More preferably, the acrylate copolymers are methyl methacrylate copolymers.

A solid component pack of an inventive bone cement formulation contains from 3 to 25 solid component pack weight percent of a polyacrylate. Preferably, the polyacrylate is polymethyl methacrylate. The polyacrylate is preferably present from 3 to 20 solid component pack weight percent. More preferably, the polyacrylate is present from 5 to 15 solid component pack weight percent. The solid component pack also contains from 60 to 97 solid weight pack weight percent of F154 high impact POLYMER CLEAR (Esschem, Inc.) where POLYMER CLEAR contains 0.38 weight percent benzoyl peroxide, 9.9 weight percent barium sulfate and 89.02 percent rubber toughened polymethyl methacrylate. An alternative inventive solid component pack for an inventive cement formulation contains 0.3 to 20 solid component pack weight percent of an elastomeric rubber toughener and a polymer bead having a polyacrylate terminated surface.

A solid component pack according to the present invention also optionally contains a radiopaque agent in order to increase the x-ray contrast of the inventive bone cement formulations. Radiopaque agents illustratively include calcium, strontium, barium, zirconium, and zinc sulfates, oxides and mixtures thereof. A radiopaque agent, if used, is present preferably from 5 to 15 solid component pack weight percent, and more preferably from 5 to 10 solid component pack weight percent.

The solid component pack of an inventive bone cement formulation also optionally includes a polymerization initiator. The initiator used herein being selected from those known in the art and consistent with the polymerizable acrylate monomer to be polymerized. Polymerization initiators operative herein illustratively include benzoyl peroxide, lauryl peroxide, methyl ethyl peroxide, diisopropyl peroxy carbonate, organometallic compounds, sulfinic acid derivatives, and tertiary amines. The tertiary amines illustratively including dimethyl amino ethyl methacrylate, triethanol amine, 4-dimethyl amino benzoic acid methyl, 4-dimethyl amino benzoic acid ethyl, and 4-dimethyl amino benzoic acid isoamyl. An initiator, if used in the solid component pack, is present from 0.3 to 3.0 solid component pack weight percent.

The solid component pack of an inventive bone cement formulation also optionally contains a biocompatibility additive. A biocompatibility additive includes antibiotics, bone morphogenetic protein, chemotherapeutic substances, hormones and mixtures thereof. These additives are selected from any of those known to the art and illustratively include gentamicin, cytostatic agents, calcitonin, aminoglycosides, cephalosporins, macrolides, and mixtures thereof. Specific antibiotics operative herein illustratively include erythromycin, lyncomycin, clyndamycin, novobiocin, vancomycin, fusidin acid, rifampicin, polymycine, neomycin, kanamycin and tobramycin. A bioactive additive, if used, is present from 0.05 to 3 solid component weight pack percent. It is appreciated that additional fillers, pigments, thixotropic agents and the like optionally are added to a solid component pack of an inventive cement formulation.

In a preferred embodiment, the solid component pack contains 93 to 98 percent of polymer bead core having polymethylmethacrylate terminated surface, 1 to 3 percent polyalkylene copolymer elastomeric rubber toughener, and 0 to 2.5 percent initiator, where percentages are weight percentages based upon solid component pack total weight percent.

An alternative preferred dry component pack of an inventive cement formulation contains 5 to 15 percent of polymethyl methacrylate admixed with Esschem F154 high impact POLYMER CLEAR.

The liquid component pack of an inventive bone cement formulation contains a polymerizable acrylate monomer. Preferably, the acrylate monomer includes at least as a portion thereof methylmethacrylate.

The liquid component pack of an inventive bone cement formulation also optionally contains an accelerator. The accelerator being chosen from those known to the art and illustratively including N,Ndimethyl-p-toluidine; N,N-hydroxypropyl-p-toluidine; and mixtures thereof. An accelerator, if used, is present from 0.2 to 3.0 liquid component pack weight percent. More preferably, accelerator if used is present from 0.4 to 1.0 liquid component pack weight percent.

The liquid component pack of an inventive bone cement formulation optionally also contains a polymerization inhibitor conventional to the art. A polymerization inhibitor operative herein illustratively includes hydroquinone, ascorbic acid, hydroquinone methyl ether and mixtures thereof. Hydroquinone is used in most commonly art and preferably used herein. A polymerization inhibitor, when used, is present from 5 to 1000 parts per million of the liquid component pack and more preferably from 20 to 100 parts per million thereof.

Preferably, an inventive liquid component pack contains 97.4 to 99.3 percent polymerizable methyl methacrylate, 0.5 to 3 weight percent N,N-dimethyl-p-toluidine, and 75 to 150 parts per million hydroquinone.

Figure 4:
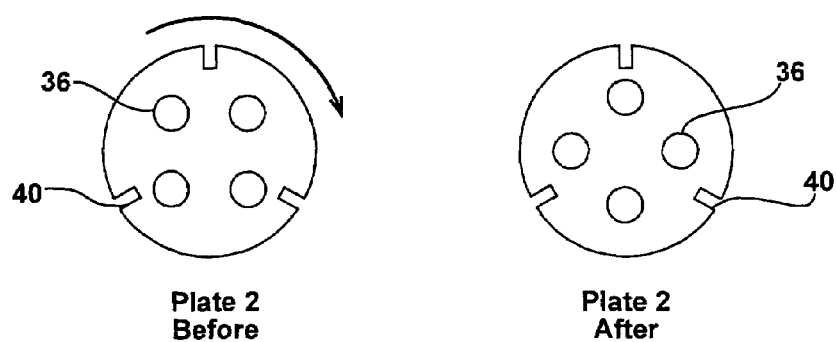
FIG. 4 is an end view illustration depicting the rotation pattern of plates 2 and 3 of the system of FIG. 1.
Figure 5:
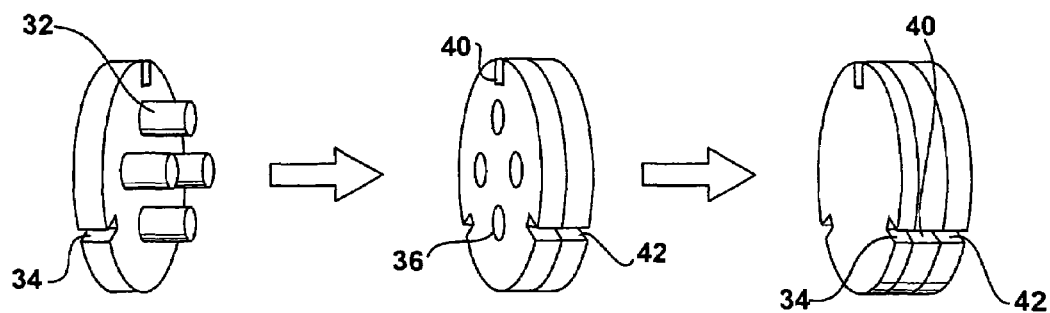
FIG. 5 is a schematic showing the engagement of plates 1, 2 and 3 upon alignment of the plates.
Figure 6:
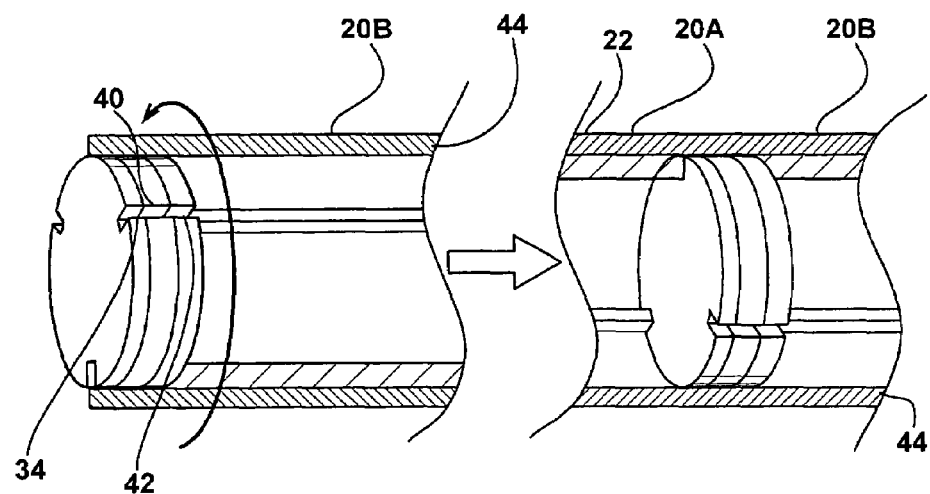
FIG. 6 is a schematic partial cutaway view illustrating the alignment of plates and tracks for cement delivery through an exit nozzle of the system depicted in FIG. 1.

The rapid mixing and delivery of a bone cement prior to gelling and substantially free of air entrainment is critical to obtaining optimal mechanical properties from a given bone cement. An inventive bone cement mixing and delivery system is illustrated in FIGS. 2-8. A cylinder tube 20 has three tracks shown collectively at 22 within the inner wall 24 of the cylinder tube. The tracks 22 are spaced at 120° intervals. Cylinder tube 20 is constructed of materials illustratively including plastic, metal and glass and serves as a container for a bone cement liquid component pack and a bone cement solid component pack. The cylinder tube 20 stores a liquid component pack in portion 20a and a solid component pack in portion 20b. It is appreciated that two portions 20a and 20b can be stored separately yet combined to produce a leakage-free seal. While it is appreciated that there are numerous methods known to the art of fluid communication for selectively sealing like inner diameter tubes, a preferred design in shown in FIG. 3. Tube portion 20a terminates in a flange 26. Tube portion 20b terminates in a face adapted to secure against flange 26 directly or with a plate therebetween. A threaded collar 28 slides over the exterior 30 of tube portion 20b and engages the terminal face 27 of tube portion 20b. A threaded fitting 32 surrounds the exterior 31 of tube portion 20a and engage the flange portion 26. The fitting 32 has threads complementary to those of fitting 28 such that upon engagement of the fitting pair 28 and 32, the flange 26 and the terminal face 27 are urged together to form a seal. The relative axial rotation between tube portions 20a and 20b upon forming a seal therebetween is appreciated to be controlled through the use of an alignment pin, lock-key or other rotational symmetry disrupting mechanical feature. Three plates mount within the tube 20. Plate 1 has four needles 32 and three notches 34 therein. Plate 1 has notches 34 spaced to engage the tracks 22 of tube portion 20a. As plate 1 moves along the length of tube portion 20a, there is no rotation of plate 1 unless tube portion 20a itself rotates. Plate 1 functions to seal a liquid component pack within tube portion 20a. Plates 2 and 3 have highly polished surfaces such that a vacuum can be maintained therebetween. Plate 2 has a series of holes 36 therein whereas plate 3 has a series of holes 38 uncoordinated from those of plate 2. Plate 2 has notches 40 fitted to the tracks 22 of tube portion 20a. Plate 3 also has a series of symmetrically spaced notches 42 and the notches of plate 3 engage a set of tracks 44 that are discontinuous with the tracks 22 of tube portion 20a, as shown in FIG. 4. Thus, when one desires to mix the liquid contents of tube portion 20a with the solid component pack of tube portion 20b, one rotates tube portion 20a relative to tube portion 20b thereby causing plate 2 to rotate relative to plate 3 thereby bringing the holes 36 of plate 2 into alignment with the holes 38 of plate 3. With hole alignment between plates 2 and 3, the liquid component pack stored in tube portion 20a can pass through the holes 36 and 38. Preferably, tube portion 20b has been previously evacuated and has a void volume equal to or greater than the volume of the liquid component pack in tube portion 20a so as to spontaneously draw all the liquid stored in tube portion 20a into tube portion 20b. Thus, the liquid component pack and the solid component pack are mixed within tube portion 20b. As the liquid component pack in tube 20a is drawn into tube portion 20b, plate 1 is pulled into contact with plate 2. The needles 32 of plate 1 penetrate the aligned holes 36 and 38, as shown in FIG. 6. The needles 32 on plate 1 serve as a stopper to prevent backward leakage of cement to tube portion 20a and also allows three plates to be rotated through an angle necessary for the notches 34, 36 and 38 along track 44 with a pressure exerted by a conventional injection gun. Preferably, the track 44 is helical along the interior 30 of tube portion 20b to facilitate mixing and uniformity. Upon removing a seal from the applicator tip portion 50 of tube portion 20b and exerting pressure on the rear face of plate 1 with an injector gun, a uniformly mixed bone cement free of entrained air bubbles is delivered through 50.

A bone cement formulation according to the present invention is detailed in the following examples. These examples are intended to only be illustrative and nonlimiting as to the scope of the invention defined by the appended claims.

EXAMPLES

Materials and Methods

Example 1—Bone Cements

Simplex P bone cement was purchased from Howmedica International Inc. LUCITONE 199 was purchased from Caulk Dentistry (Milford, Del.). This particular impact modified acrylic powder is a copolymer of methyl methacrylate with butadiene and styrene, which is then coated with PMMA. F154 High Impact Polymer Clear (Esschem) was obtained from Esschem Inc. (Linwood, Pa.). This particular polymer is a rubber modified PMMA that is used as a denture base in the dental field. It contains 0.38% benzoyl peroxide (BPO). The particle size is 1% on 80 mesh, 1.5% on 100 mesh, 8.6 on 150 mesh, 36.4% on 250 mesh, and 52.4% on pan. Coe-Tray PMMA (assigned as PMMA) was purchased from GC America Inc. (Chicago, Ill.). In addition, Polybutene (PB) (Mw=9,000 g/mol from GPC measurements, Macomer, Revertex Ltd. Harlow UK), a copolymer of isobutylene-butene, which consists predominately of high molecular weight polyolefins with minor isoparaffin content, was also used in formulation. Barium sulfate ($BaSO_4$), a radiopaque agent, was purchased from Acros Chemical Company. Benzoyl peroxide (BPO), hydroquinone (HQ) and methyl methacrylate (MMA, inhibited with 25 ppm±5 ppm HQ) were purchased from Fisher Scientific. N,N-Dimethyl-p-toluidine (N,N-DMPT) was purchased from Aldrich Chemical Company with a purity of 99%. All the chemicals were used as received and without further purification.

Example 2—Residual Monomer

A Perkin Elmer Sigma 3B GC with a Supelco 10% SP-2100 80/100 mesh column was employed to measure the residual monomer. A flame ionization detector was used to quantify the residual monomer amount. The injector, column and detector ports were set at 200, 185 and 190° C., respectively. The flow rates of helium, hydrogen and air were adjusted so both MMA and EMA gave narrowest peak widths and noticeably different elution times. The method employed a pentane or methylene chloride extraction of ground cement powder, since the residual monomer is soluble in pentane but PMMA is not soluble. Methylmethacrylate (MMA) and ethylmethacrylate (EMA) in pentane solutions were used to calibrate the instrument and EMA was used as an internal standard. A 1 µl sample was injected into the gas chromatograph. The ratio of the MMA to the EMA was determined by the height of the corresponding peaks from each of the chromatogram. The monomer content in the bone cement specimen was determined from the calibration curve constructed from detector response factors obtained from a series of standard solution containing various amount of MMA and fix amount of EMA. Each specimen was collected as three samples from different areas of the specimens and each sample was measured in triplicate.

Example 3—Size Exclusion Chromatography (SEC)

The molecular weight and molecular weight distributions were determined in both the powder and the formulated cements using a customer made Waters size exclusion chromatography. A Waters HPLC pump (Waters, Model 590) was used for eluent delivery at 1.0 mL/min. A Waters 410 differential refractometer was used as a concentration detector. The instrument was running at 25° C. and equipped with three Waters Ultrastyragel HR3, HR4, and HR5 columns (Waters Corp. Milford, Mass.), measuring 30 cm in length and packed with 5 µm diameter PS Gel. The THF solvent was filtered and degassed before use. Samples were dissolved in THF at a concentration of 0.2~0.4 mg/mL and preferably centrifuged before filtered with 0.2 µm pore size poly(tetrafluoroethylene) membrane filters (some rubber and radiopaque components could not be dissolved in THF). Injection volumes of 100 µL were used. TriSEC software (Viscotek Co.) was used for data treatment. A series of eleven PMMA standards (Pressure Chemical Pittsburgh, Pa.) with their molecular weights ranging from 6000 to 1,600,000 were used to generate the calibration curve.

Example 4—Thermal Analysis

Differential scanning calorimetric analysis (DSC) was performed on a Mettler thermal analysis system with TC15 controller (Mettler Toledo, Columbus, Ohio). Nitrogen atmosphere was applied.

Example 5—Hand Mixing

A series of formulations were prepared and compared with the commercial bone cement formation Simplex P. The redox initiator was blended with powder component and the redox accelerator was added to MMA monomer. The room temperature powder and liquid components were added to a Stryker high vacuum cement injection system and mixed for 2 minutes followed by the transferring the dough under partial vacuum to a cartridge and then injected into stainless steel molds for specimen formation.

Example 6—Tensile Testing

Specimens were prepared using the Stryker Advanced Cement Mixing System. A double batch of cement was mixed and injected into the tensile mold. After the cement cured, "dog-bone" specimens (central reduced section) were removed from the mold and placed in deionized water at 37° C. for 24 hours or 7 days.

Using a Sintech 2/G Screw Machine for testing, specimens were placed in the grips taking care to align the long axis of the specimen and grips in the same vertical plane. A 1.3 kN range load cell was used to measure the applied load, global displacement was measured using the machine actuator displacement, and gage length displacement was measured using an externally applied extensometer. Specimens were loaded to failure in uniaxial tension at a rate of 5 mm/min. The specimens were tested in air at room temperature immediately after removing them from the deionized water bath.

The tensile strength of the specimens was calculated by dividing the maximum applied load by the original minimum cross-sectional area of the reduced section of the specimen. The tensile modulus was calculated as the slope of the linear portion of the tensile stress-strain curve. The % elongation was calculated as the change in gage length divided by the original gage length. Finally, the toughness was calculated as the area under the stress-strain curve.

After testing, the fracture surface of the specimens was examined for any voids. Only specimens with voids less than 1 mm in diameter were included since the interest was in the material properties of the bone cement. Since the strength of the bone cement is highly dependent on the size of the defects at the fracture surface, specimens with large voids would have a much lower tensile strength, tensile modulus, % elongation, and toughness, therefore, not a true representation of the material properties.

Example 7—Compressive Strength

Using the Stryker Advanced Cement Mixing System, a single unit of cement was mixed and injected into the compression mold. After the cement had cured for 1 hour, cylindrical specimens (6 mm in diameter and 12 mm in height) were removed from the mold and placed in deionized water at 37° C. for 24 hours or 7 days.

Mechanical testing was performed using a Sintech 2/G Screw Machine with computer data acquisition and analysis. Specimens were placed in the fixture and tested to failure at a rate of 25.4 mm/min. They were tested immediately after removing them from the deionized water bath. Global displacement was measured using the machine actuator displacement.

The compressive strength of the specimens was calculated by dividing the load at failure by the original cross-sectional area of the cylinder. The load at failure was the 2% offset load. The compressive modulus was calculated as the slope of the linear portion of the compressive stress-strain curve.

Example 8—Fracture Toughness

A double batch of cement was mixed in a Stryker Advanced Cement Mixing System. The cement was injected into a stainless steel rectangular mold with a center notch and allowed to cure under pressure. Then the block was machined to produce single edge-notched specimens with final dimensions of 6 mm W×12.5 mm T×63 mm L. All specimens were aged in deionized water at 37° C. for 24 hours or 7 days before testing.

Testing was performed using a Sintech 2/G Screw Machine. A sharp crack was introduced in the single edge-notched specimen immediately before testing. The samples were tested at a crosshead speed of 0.5 mm/min. Load versus displacement graphs were recorded, and the maximum load at fracture was measured for each specimen and used to calculate the fracture toughness.

Example 9—Formulations

Various formulations based on LUCITONE are shown in Table 1.

TABLE 1

Various Lucitone Formulations

| Formulation 1 Plain Lucitone | | Formulation 2 PB Modified Lucitone | | Formulation 3 γ-Irradiated Lucitone | |
|---|---|---|---|---|---|
| | g | | g | | g |
| Lucitone 199 | 65.8 | Lucitone 199 (or PMMA) | 65.1 | Lucitone 199 | 36.0 |
| | | Polybutene | 1.0 | $BaSO_4$ | 4.0 |
| Benzoyl peroxide | 0.65 | Benzoyl peroxide | 0.65 | Benzoyl peroxide | 0.405 |
| Methyl methacrylate | 32.9 | Methyl methacrylate | 32.6 | Methyl methacrylate | 18.0 |
| N, N-DMPT | 0.65 | N, N-DMPT | 0.65 | N, N-DMPT | 0.45 |

The handling properties of γ irradiated LUCITONE based cement formulation was further improved. In addition, the dispersion ability of the radiopaque agent $BaSO_4$ was improved. In some preliminary formulations incorporating $BaSO_4$ and non-irradiated LUCITONE, the dispersion of $BaSO_4$ was very difficult, showing agglomeration and lack of wetting. The difficulty was overcome by blending the solid components in a Waring blender, followed by removal of clumps with a 350 μm sieve. The irradiated LUCITONE, with its low molecular weight, exhibits better handling characteristics including easier dispersion of $BaSO_4$.

Example 10—Molecular Weights

Molecular weight and molecular weight distribution of the bone cement before and after cured are listed in Table 2.

TABLE 2

Molecular Weight and Residual Monomer Contents of Lucitone-Based Cements

| Sample Code | $M_w \times 10^{-3}$ | $M_n \times 10^{-3}$ | $M_w/M_n$ | Residue (%) |
|---|---|---|---|---|
| Simplex P | 215 | 89 | 2.42 | 7.86 |
| LCT | 379 | 150 | 2.54 | 2.49 |
| LCT rad | 173 | 78 | 2.22 | |
| Simplex P formulation | 234 (4.3) | 90.5 (9.3) | 2.59 | 3.88 (0.93) |
| LCT formulation | 440 (33.5) | 140 (12.1) | 3.14 | 3.29 (0.256) |
| LCT/PB formulation | 352 (8.54) | 142 (2.42) | 2.48 | 1.81 (0.47) |
| LCT/rad formulation | 182 (1.84) | 89 (1.41) | 2.04 | |

Different formulations resulted in tremendous molecular weight variation based on SEC chromatograms. Pure LUCITONE formulation had the highest molecular weight (about 224,000), much greater than that of the Simplex P control (about 160,000). The molecular weight of the PB modified LUCITONE formulation is very close to the molecular weight of the pure LUCITONE formulation. The γ irradiated LUCITONE exhibits molecular weights very close to that of the Simplex P formulation.

More apparent difference is observed when the molecular weight distributions are compared. A γ irradiated LUCITONE formulation shows very uniform molecular weight distribution. Molecular weight distribution of pure LUCITONE, on the other hand, shows a bimodal behavior, which is more uniform than prior art DRG cements.

The bimodal behavior of molecular weight distribution of the cements is caused by different molecular weights of PMMA powder and newly polymerized matrix. There is an apparent change in the average molecular weight during curing. The inter-bead matrix has a different average molecular weight than the pre-polymerized beads.

The molecular weight distributions of the inventive cements became more uniform when 1% of polybutene is added. Comparing the molecular weights and molecular weight distribution of PB modified LUCITONE and pure LUCITONE cement, the gel effect for PB modified LUCITONE is not as pronounced as that in the pure LUCITONE formulation. Furthermore, the molecular weight of newly formed irradiated LUCITONE was the smallest of the discussed formulations.

Example 11—Reactivity of Elastomeric Rubber Toughener Towards Polyacrylate Addition To examine whether or not polybutene, which has "reactive" unsaturated end groups, was covalently bonded into the cement, extractions were conducted using hexanes. A substantial amount of polybutene was isolated of Table 1, Formulation 2 from the cement (SEC analysis). This result shows that substantial amounts of polybutene are not covalently bound into the acrylic cement but instead are physically dispersed therein.

Example 12—Residual Monomer

A gas chromatography method was employed to determine the residual monomer content. During the measurements, the gas pressure and the temperature of the different compartments were optimized to obtain the best peak resolution and signal/noise ratio. A typical chromatogram shows three peaks. Shortly after the n-pentane peak is the peak representing impurities in the solvent, followed by the peaks of MMA and EMA. The calibration curve shows a linear relation between the peak height and MMA content. Usually, the method with 5 points of regression generates a curve with regression coefficient greater than 0.998. The residual monomer of the bone cement was determined by measurement of extracted solution of bone cement. The residual monomer of the experimental bone cement and the Simplex control are shown in Table 1. From Table 1, indicating that the residual monomer contents of experimental bone cements are systematically lower than that of Simplex P control.

In the GC method, the residual monomer was measured and calculated based on the total mass of the specimens. In a bone cement system, polymer powder was not completely dissolved in monomer to form a homogeneous phase during the mixing. Any undissolved PMMA powder would be part of the total mass but not part of the reaction mass. For two bone cement formulations, even the residual monomer content of the reaction mass were the same, if the reaction mass ratio to the total mass had been smaller, the total amount of residual MMA also would have been lower since the powder had a very low residual monomer content. Depending on the dissolution characteristics of the particular cement, undissolved powder could account for over half of the total mass of the material, based on Kusy's estimation. Comparing the residual monomer content of Simplex P, LUCITONE and PB modified LUCITONE, the higher the rubber content in the cement formulation, the lower the residual monomer. The presence of PB reduces the uptake of MMA into the powder matrix.

In addition to the potential effects on mechanical properties, the presence of residual monomer has an adverse effect on the vicinal cell tissue around the bone cement.

Example 13—Mechanical Properties

Mechanical properties of inventive bone cements and the Control are listed in Table 3.

TABLE 3

Mechanical properties of the modified bone cements and Simplex P cement

| Composition | Flexure (MPw) | Flexure Displacement | Notched Flexure (MPa) | Compression | Elastic Modulus (GPa) |
|---|---|---|---|---|---|
| Simplex | 66.60 (4.8) | 7.87 (0.59) | 39.1 (4.1) | 85.7 (4.9) | 1.93 (0.11) |
| Lucitone 199 | 61.32 (4.5) | 9.65 (1.2) | 54.9 (8.99) | 76.3 (4.9) | 1.74 (0.10) |
| PB modified Lucitone 199 | 73.71 (2.64) | 11.60 (0.7) | | 84.9 (2.6) | 1.87 (0.11) |
| PB modified PMMA | 57.44 (3.5) | 5.5 (0.7) | | 84.9 (2.6) | 1.98 (0.18) |
| Lucitone Rad | 84.7 (6.58) | 13.01 (8.8) | | 91.33 (1.93) | 2.33 (0.21) |

Incorporating rubber toughened PMMA substantially increases the fracture toughness of bone cement. The plain LUCITONE group exhibited improved notched flexure strength and greater displacement over Simplex P control before fracture in the flexure test.

The most striking difference between the inventive formulations and the conventional PMMA formulation is that many test bars from LUCITONE based formation did not break when the flexure test was performed. The toughened material underwent complete yielding. This behavior is strong evidence that toughened material exists in the formulation.

In the bone cement formulation, as discussed above, the powder component was not totally dissolved in monomer before setting. There is a clear interface between the powder and the newly formed PMMA phase.

Both mechanisms can be observed from the surface of the broken specimen of notched fracture testing either by microscopy or by using a magnifying glass. A Simplex P specimen showed flat propagation of the crack with a smooth fracture surface morphology. Clearly, PMMA particles exhibited brittle fracture and appeared to have been cleaved. For the LUCITONE formulation, the appearance of the fracture surface of the inventive cement was more irregular showing smooth and rough regions. The crack propagation path moved preferentially through the interbead matrix (newly formed PMMA) and fewer fractured beads are observed. In the smooth regions, the crack propagated directly through the beads and matrix fracturing the particles. In the rough region the mechanism changed to ductile tearing. The increase of plastic deformation of the cement matrix with rubber content could be detected macroscopically because the plastically deformed zone ahead of the crack tip became whiter than the rest of the specimen.

Figure 7:
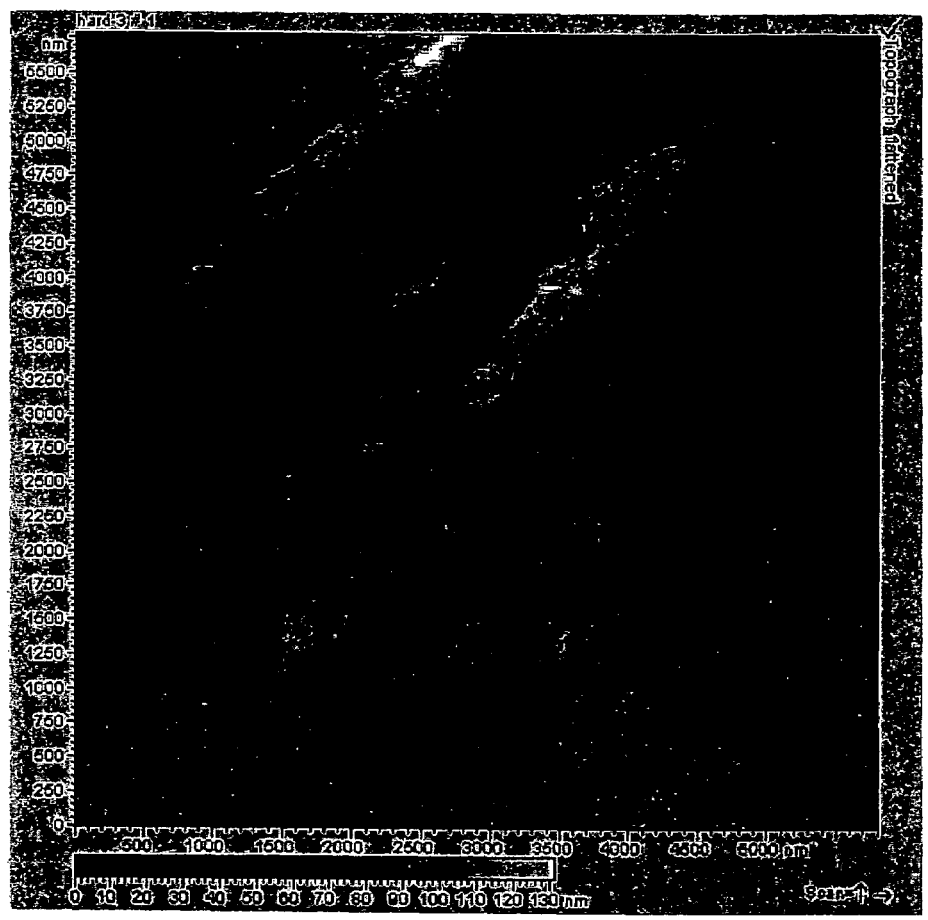
FIG. 7 is an atomic force microscopy image depicting a fracture surface of a conventional bone cement depicting a brittle breakage structure.
Figure 8:
FIG. 8 is an atomic force microscopy image depicting a fracture structure conventional bone cement depicting a craze structure.
Figure 9:
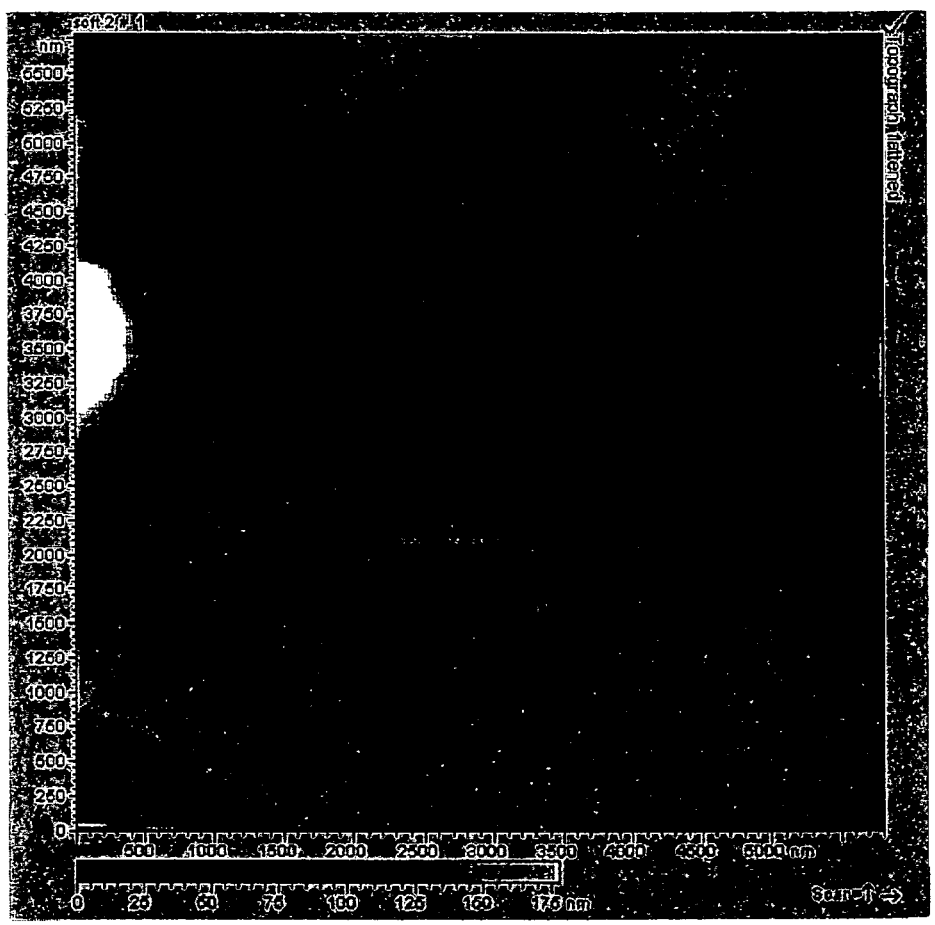
FIG. 9 is an atomic force microscopy image of an inventive bone cement depicting ductile tearing structure.
Figure 10:
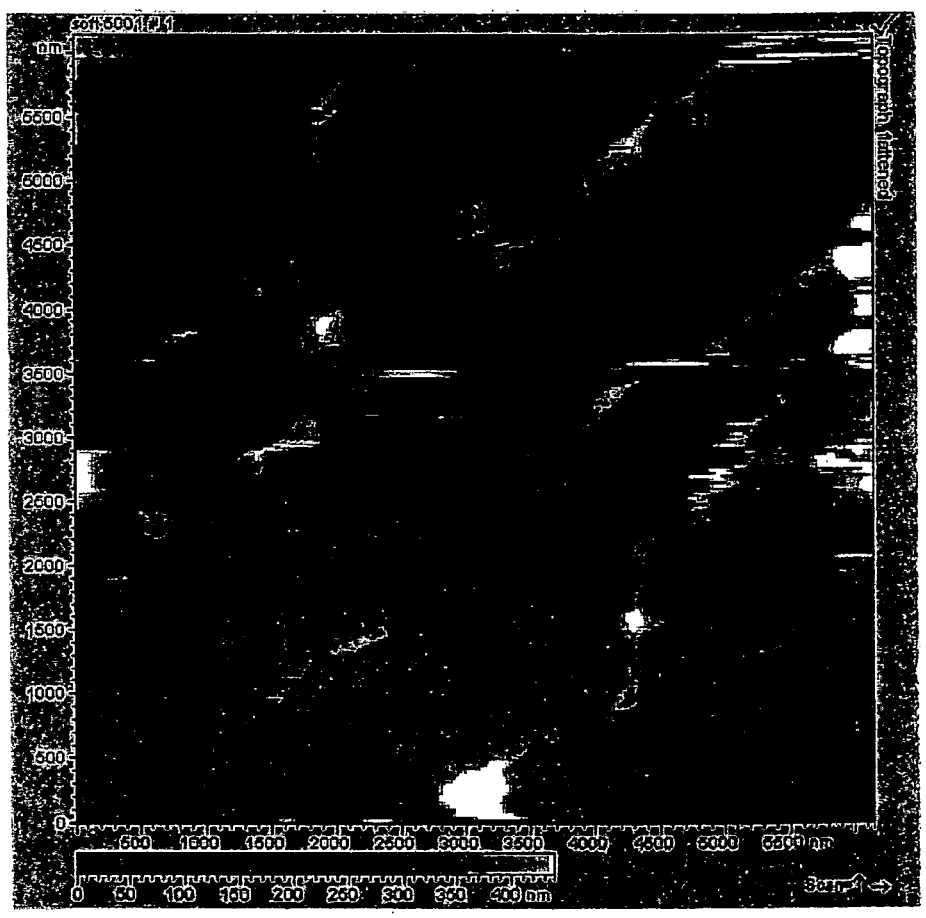
FIG. 10 is an atomic force microscopy image of an inventive bone cement depicting an elastic structure.

AFM fractographs of conventional and rubber toughened bone cement are shown in FIG. 7 through FIG. 10. Compared to conventional SEM fractographs, AFM fractographs reveal more details about the structure of the surface in 3-dimensional expression. FIG. 7 is the fracture surface of the conventional bone cement. A relatively flat surface can be observed, reflecting a brittle breakage mechanism. The surface texture was very much similar to that of flour dough that was pulled apart. A crazed structure can be seen in FIG. 8. The craze was parallel to the crack surface. The width of the fiber was about 5 μm. The fiber was not perfect but contained holes, reflecting the three dimensional strength. When the bone cement was toughened by the addition of rubbery material, a brush-like structure can be observed (FIG. 9), which was presumably caused by the ductile tearing of the matrix. The brush hairs were inevitably almost perpendicular to the crack surface. The most apparent difference of the brush hairs as compared to the other structure was that the hairs were very much like carrots with smooth surface and cylinder shape. The diameter of the cylinder was about 2 μm. Such structures were not observed for un-toughened material; however, it was widely dispersed in the toughened materials. Elastic structure can be observed from the toughened material as shown in FIG. 10.

Although the ductile material was increased in the formulation, the flexure and compressive strength of LUCITONE, however, were only 8% and 11% lower than that of Simplex P formulation, and the difference was statistically significant. This trend is consistent with the results of Vila et al. for ABS toughened bone cement. However, the reduction of the properties was not as significant as in Vila's formulation. As expected, the autopolymerized materials have significantly reduced values of flexure and compressive strength and elastic modulus as compared to commercially extruded PMMA rod. LUCITONE based inventive formulation powder beads are smaller and the interface is less noticeable. The adhesion force of smaller beads between the interfaces should be greater than that of the large beads, as compared to prior art DRG formulations.

It was discovered that the mechanical properties of PB modified LUCITONE were further improved over that of plain LUCITONE formulations. Flexure strength, flexure displacement, compressive strength and elastic modulus of inventive PB modified LUCITONE are greatly improved as compared to pure LUCITONE formulations. Obviously, these effects cannot be explained by the rubber toughened mechanism since the addition of PB will make the material more ductile and lower tensile and comprisal strength.

As a reference, PB modified PMMA (Coe-tray) formulations were prepared. Many mechanical properties of PB modified PMMA were inferior to those of the pure LUCITONE or Simplex P formulations. However, compressive strength and elastic modulus of PB modified PMMA are impressively high. Both properties are important in bone cement formulation since the bone cements are required to withstand considerable compressive forces. The cement should be able to transmit the imposed loads without failure during the lifetime inside the human body.

Example 14—Composition of SIMPLEX and Esschem Based Inventive Bone Cement Formulations In order to obtain novel bone cements, which have mechanical and chemical properties, superior to those of existing commercial PMMA-based formulations but with good handling properties, new formulations based on the rubber-toughened approach were designed but with different starting materials. Denture base resin Esschem was used in this formulation to improve the overall properties of Simplex P bone cement. The description of the base prior art compositions is listed in Table 4. The inventive formulations based on the Esschem and Simplex P resins are listed in Table 5.

TABLE 4

Composition of Prior Art Base Esschem and Simplex P Bone Cement Formulations

| Constituent | Composition wt. % | |
| --- | --- | --- |
| | Simplex P | Esschem |
| Powder | | |
| BPO | 1.19 | 1.09 |
| $BaSO_4$ | 10.00 | 9.90 |
| PMMA | 16.55 | |
| Rubber toughened PMMA | | 89.02 |
| P(MMA/ST) | 72.26 | |
| Liquid | S | E |
| N,N-DMPT | 2.48 | 2.43 |
| Hydroquinone | 75 ppm | 125 or 75 ppm |
| MMA | 97.51 | 97.55 |

TABLE 5

Weight of the each component in inventive formulations

| | | | | | Liquid E | |
| --- | --- | --- | --- | --- | --- | --- |
| Sample Code | Description | Simplex P (g) | Esschem (g) | Coe-Tray PMMA (g) | Liquid S (g) | 75 ppm HQ (g) | 125 ppm HQ (g) |
| S | Simplex P | 80 | 0 | 0 | 40 | 0 | 0 |
| S5E | Simplex P 5% Esschem | 76 | 4 | 0 | 40 | 0 | 0 |
| S10E | Simplex P 10% Esschem | 72 | 8 | 0 | 40 | 0 | 0 |

TABLE 5-continued

Weight of the each component in inventive formulations

| | | | | | Liquid E | |
|---|---|---|---|---|---|---|
| Sample Code | Description | Simplex P (g) | Esschem (g) | Coe-Tray PMMA (g) | Liquid S (g) | 75 ppm HQ (g) | 125 ppm HQ (g) |
| E46-0 | Ess-46 | 0 | 80 | 0 | 0 | 0 | 46 |
| E40-0 | Ess-46 | 0 | 80 | 0 | 0 | 40 | 0 |
| 46-5P | Ess-46.5% PMMA | 0 | 76 | 4 | 0 | 0 | 46 |
| E40-5P | Ess-40.5% PMMA | 0 | 76 | 4 | 0 | 40 | 0 |

Example 15—Mixing Properties

A series of different compositions of Simplex P and Esschem resins are formulated based on the ratios listed in Table 5. Their mixing and handling properties are summarized in Table 6. The dough times, setting times and maximum temperatures are listed in Table 7.

TABLE 6

Summary of Mixing and Handling Properties of Inventive Bone Cement Formulations

| Sample | Initial Appearance Description | Time | Time to Become Homogeneous | Initial Viscosity Increase | Transfer |
|---|---|---|---|---|---|
| S | Powdery clumps | 0-45 sec | 45 sec | >1 min | 3 |
| S5E | Powdery | 0-40 sec | 40 sec | >1 min | 3 |
| S10E | Powdery, fluid | 0-30 sec | 30 sec | >1 min | 3 |
| E46-0 | Center clumpy, fluid | 0-1 min | 1 min | >1 min | 2 |
| E40-0 | Very clumpy | 0-2 min | — | 45 sec | 4 |
| E46-5P | Smooth, fluid | 0-1 min | 10 sec | >1 min | 1 |
| E40-5P | Center clumpy | 0-2 min | — | >1 min | 2 |
| E46-10P | Center clumpy | 0-1 min | 1 min | — | 1 |
| E40-10P | Slightly clumpy | 0-2 min | — | >1 min | 2 |
| E46-15P | Powdery clumps | 0-1 min | 1 min | — | 2 |
| E40-15P | Center clumpy | 0-1 min | 1 min | >1 min | 2 |

Degree of difficulty during transfer
1. Transfer easy (transfer required stirring)
2. Transfer moderate (transfer required using the vacuum and stirring)
3. Transfer difficult (transfer required using the vacuum, stirring and tapping on the bench top)
4. Transfer very difficulty (some bone cement was left in bowl even with using the vacuum, stirring, and tapping the mixer on the bench top.)

TABLE 7

Physical Properties of Experimental Bone Cement Formulations

| Bone Cement | Dough Time (min) | Temperature$_{max}$ (° C.) | Setting Time (min.) |
|---|---|---|---|
| S (prior art) | 4.50 (0.00) | 77.80 (4.92) | 10.98 (0.57) |
| S5E | 4.88 (0.53) | 80.95 (12.23) | 11.25 (3.22) |
| S10E | 4.25 | 67.20 | 11.20 |
| E46-0 (prior art) | 12.31 (2.38) | 64.27 (5.25) | 16.71 (3.25) |
| E40-0 (prior art) | 8.56 (0.63) | 62.37 (1.64) | 14.57 (1.38) |
| E46-5P | 12.25 (1.77) | 67.2 | 17.08 |
| E40-5P | 9.88 (0.18) | 60.55 (2.05) | 15.73 (1.14) |
| E46-15P | 10.75 (1.09) | 69.75 (2.33) | 16.43 (0.86) |
| E40-15P | 9.13 (0.88) | 67.40 (9.90) | 13.31 (0.34) |

The experimental cement formulations mixed in a similar manner to Simplex P using the Stryker mixing apparatus. The mixing properties showed notable differences. The 2:1 powder to liquid (P/L) ratio pure Esschem cement (E40-0) resulted in a higher viscosity mix that did not possess a smooth consistency. In addition, it did not readily transfer to the injection cartridge, leaving material on the stirring blade and walls of the mixer. As reported in Table 7, the setting time and maximum temperature met ISO or ASTM specifications.

To improve the mixing, a lower P/L ratio was investigated. A ratio of 1.74/1 powder/liquid formulation was used (E46-0). By decreasing the P/L ratio the viscosity of the mix decreased and the consistency became very smooth after 1 minute of mixing. Likewise, the transfer to the injection cartridge was much easier, only requiring stirring to transfer the cement. With the increase in monomer content the cement stayed fluid too long.

Next, three different weight percents of PMMA were added to Esschem, 5, 10 and 15% (E40-5P, E46-5P, E40-10P, E46-10P, E40-15P, and E46-15P). As the percentage of PMMA increased the time required for the material to become homogeneous decreased, the dough time decreased, and the setting time decreased.

By modifying standard commercial orthopedic bone cement with 5 or 10 weight percent rubber toughened polymer, mixing and handling properties remain basically unchanged. There was no significant difference in physical properties such as dough time, maximum temperature, or setting time when compared to Simplex P. Actually, the time it took the cement to become homogeneous was decreased with the addition of 5 or 10% Esschem. Dough time of the experimental formulations occurred between 8 and 12 minutes as compared to 4.5 minutes for Simplex P. Setting time also increased from 11 minutes for Simplex P to 13-18 minutes for the experimental formulations. The inventive material appeared to be more temperature sensitive at elevated temperatures causing a significant reduction in setting time, usually less than 8 minutes. However, the maximum temperatures of the experimental formulations were consistently less than Simplex P.

The temperature evolution during polymerization depends on the rate of heat production and the rate of heat transference to the surroundings through the conduction, radiation and convection. Shown in Table 8, an increasing L/P ratio increased the inhibitor/initiator ratio, which delays the beginning of the polymerization process. The maximum temperature attained also increased with the L/P ratio. There also is a correlation between the maximum temperature and the dough time and setting time, in that the higher the maximum temperature, the shorter the dough time and setting time.

Example 16—Molecular Weights and Residual Monomer

Clinically, all bone cements must be sterilized before use. Usually, a 2.5 Mrad γ irradiation or ethylene oxide is applied to sterilize the liquid and powder component after exposure to γ radiation; many properties of bone cement may decrease. Among these properties, the weight average molecular weight (Mw), number average molecular weight (Mn), and molecular weight distribution (MWD) are reduced significantly after γ irradiation, as shown in Table 8. However, if polymer originated from the same batch of raw powder, the molecular weight differences for different batches of γ irradiated are not significant as shown in Table 9. This means that if the sterilization procedure is properly applied, consistent properties of powder can be obtained from different batches. In order to be in consistent in clinical practice, powder components used in the inventive formulations were sterilized by γ irradiated before use.

TABLE 8

Molecular weights, molecular weight distribution and residual monomer content of bone cements and their raw materials.

| Materials | Mn | Mw | Mw/Mn | Residual Monomer |
|---|---|---|---|---|
| Plexiglass DRG (Prior Art) | 51.2 | 119 | 2.32 | 0.445 |
| Simplex P Powder (Prior Art) | 88.8 | 215 | 2.42 | 8.43 |
| Esschem Powder (Prior Art) | 213 | 636 | 2.98 | / |
| Esschem Powder Irradiated (Prior Art) | 93.0 (2.9) | 179 (0.9) | 1.92 | / |
| Coe-Tray PMMA (Prior Art) | 172 | 322 | 2.22 | |
| S (Prior Art) | 68.1 | 169 | 2.48 | 3.832 |

TABLE 8-continued

Molecular weights, molecular weight distribution and residual monomer content of bone cements and their raw materials.

| Materials | Mn | Mw | Mw/Mn | Residual Monomer |
|---|---|---|---|---|
| S5E (Prior Art) | 88.0 | 207 | 2.35 | 3.723 |
| S10E (Prior Art) | 98.4 | 263 | 2.68 | 3.348 |
| E40-0 (Prior Art) | 84.7 | 233 | 2.75 | 3.014 |
| E46-0 (Prior Art) | 85.6 | 252 | 2.94 | 3.332 |
| E40-5P | 72.7 | 218 | 2.99 | 3.037 |
| E46-5P | 83.6 | 233 | 2.78 | 3.278 |
| E40-10P | 75.7 | 232 | 3.07 | 2.789 |
| E46-10P | 107 | 278 | 2.60 | 3.035 |
| E40-15P | 85.7 | 234 | 2.73 | 3.034 |
| E46-15P | 88.5 | 248 | 2.80 | 3.234 |

TABLE 9

Molecular weight of Esschem powder after sterilization

| Batch No. | Mn (×10³) | Mw (×10³) | Mw/Mn |
|---|---|---|---|
| 98080601 | 93.6 | 181 | 1.93 |
| 98091802 | 89.7 | 179 | 2.00 |
| 98091803 | 93.4 | 179 | 1.91 |
| 98092101 | 98.6 | 179 | 1.81 |
| 98092501 | 90.0 | 179 | 1.99 |
| 98092901 | 93.7 | 178 | 1.90 |
| Average | 93.2 | 179 | 1.92 |
| Standard Deviation | 3.23 | 0.98 | 0.069 |

Molecular weight and molecular weight distribution information on different inventive bone cement formulations are listed in Table 8.

Theoretically, the higher the molecular weight, the higher the viscosity of the system, and therefore the mixing and handling should be worse. However, since the powder does not dissolve in monomer completely, mixing and handling properties are also dependent on the particle size of powder, wetting ability of powder in monomer and human operation, etc. In fact, the mixing and handling properties were improved when 5 or 10% of Esschem (S5E and S10#), which has higher molecular weight and contains a less compatible rubber, was added to Simplex P formulation.

Figure 11:
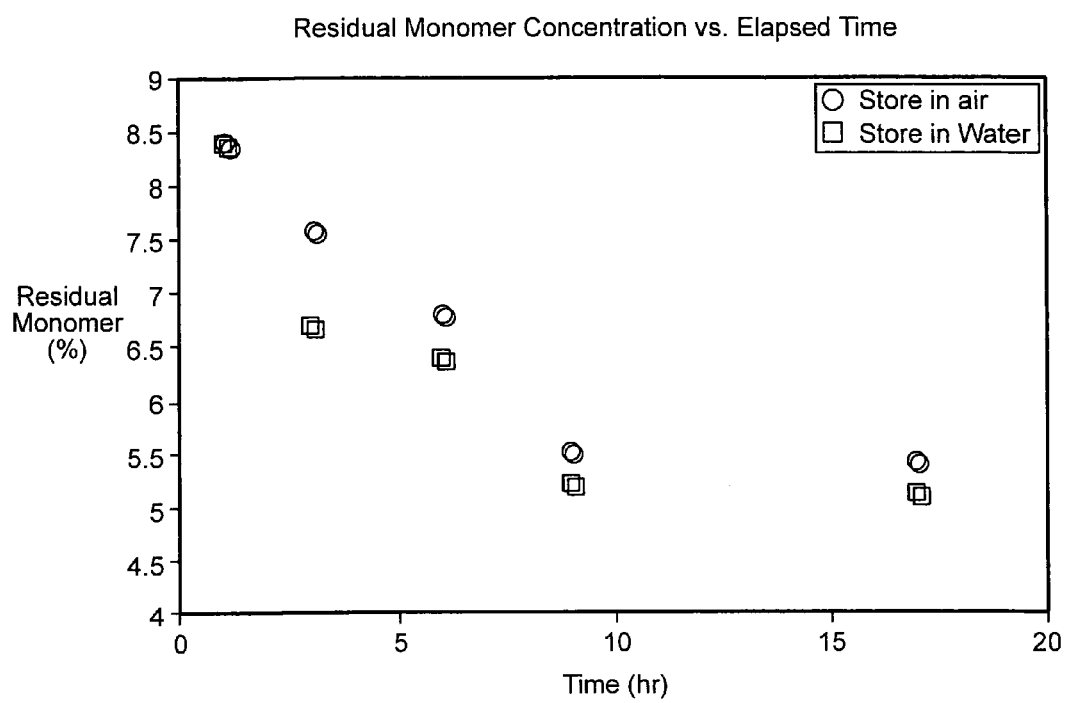
FIG. 11 is a graph of residual monomer as a function of time in an inventive bone cement.

FIG. 11 shows that for sample S5E the amount of residual monomer reaches to its stable level quickly and thus cell toxicity is expected to be low. The residual monomer amount was slightly lower in 37° C. water than that in air and their difference remained constant over 5 to 20 hours of storage time. These results demonstrate that hardened bone cement contains unreacted monomer that at its surface can be evaporated or leached out. The diffusion rate of residual monomer from inside the specimen to its surface is relatively slow. After monomer near the surface is leached out completely, the rate of monomer release to the surrounding environment slows down.

Example 17—Thermal Properties

Glass transition temperature (Tg) of Esschem after irradiation was 106° C., which is the characteristic Tg of PMMA. Tg of cured Esschem (E40-0) was 91° C. Upon heating the cement sample at 200° C. for 30 minutes under nitrogen and running the DSC again, Tg returned to 105° C. The above observations suggest that the major component of Esschem is PMMA. Tg of cured specimens were lower than Tg of PMMA. However, it can be brought back to its original temperature if the specimen was heated for a period of time. This suggests that the residual monomer in the cement serves as plasticizer to reduce the Tg of PMMA. After treatment at 200° C. the cement contained undetectable residual monomer. Since the isothermal DSC thermogram shows exothermic behavior, the post-curing reaction dominated rather than the evaporation of monomer.

Rubber cannot be detected by DSC because of its low percentage. Since the Tg of the resin was not influenced by rubber, it is surmised that rubber is immiscible with PMMA. The rubber domains enable the cement to adsorb more energy without breaking than for pure PMMA alone.

TGA thermograms of EssChem show two steps of mass loss that can be assigned to the mass loss of rubber and PMMA. The final weight did not go to zero because the degradation temperature of $BaSO_4$ is beyond the experimental temperatures employed.

Example 18—Tensile Testing

As shown in Table 10, there were no statistically significant differences in tensile strength, tensile modulus, % elongation, or toughness between Simplex P, Simplex P with 5% Esschem (S5E), and Simplex P with 10% Esschem (S10E). However, tensile properties did appear to increase upon addition of Esschem to Simplex P. When comparing Simplex P with 5% Esschem to Simplex P, there was a 19% increase in tensile strength an 8% increase in tensile modulus, a 43% increase in % elongation, and a 78% increase in toughness. Likewise comparing Simplex P with 10% Esschem to Simplex P there was a 25% increase in tensile strength, an 11% increase in tensile modulus, a 70% increase in % elongation, and a 139% increase in toughness. The influence on the mechanical behavior of adding rubber toughened PMMA can be clearly observed from tensile strength measurements.

TABLE 10

Comparison of Results from Tensile Testing

| Sample | Tensile Strength Mpa | Tensile Modulus Gpa | % Elongation mm/mm | Toughness N · mm |
|---|---|---|---|---|
| S (prior art) | 44.12 (8.33) | 2.70 (0.35) | 2.03 (0.64) | 304.53 (172.82) |
| S5E | 52.56 (2.49) | 2.91 (0.11) | 2.90 (0.47) | 541.97 (134.87) |
| S10E | 55.14 (1.76) | 2.99 (0.01) | 3.45 (0.62) | 726.50 (202.13) |

Example 19—Compressive Strength Determination

Compressive properties are important to bone cements since bone cement serves as the intermediate to transfer load between bone and prosthesis. It must therefore withstand considerable compressive force. Results in Table 11 show that all rubber toughened experimental formulations meet the compression standard for bone cement as specified in ISO Standard 5833 and ASTM Standard F 451.

TABLE 11

Comparison of Results from Compression Testing

| Bone Cement | Number of Specimens (n) | | Compressive Modulus (GPa) | | Compressive Strength (MPa) | |
|---|---|---|---|---|---|---|
| | 24 hours | 7 days | 24 hours | 7 days | 24 hours | 7 days |
| S (prior art) | 26 | 24 | 2.55 (0.14) | 2.55 (0.06) | 105.3 (9.15) | 104.3 (8.44) |
| E46-0 (prior art) | 23 | 25 | 2.13 (0.05) | 2.23 (0.04) | 84.20 (2.82) | 89.16 (4.30) |
| E40-0 (prior art) | 28 | 29 | 2.15 (0.06) | 2.14 (0.08) | 87.96 (2.43) | 88.96 (4.48) |
| E46-5P | 21 | 12 | 2.25 (0.05) | 2.27 (0.04) | 88.39 (3.52) | 91.85 (4.39) |
| E40-5P | 7 | 9 | 2.12 (0.03) | 2.27 (0.02) | 89.31 (1.01) | 95.63 (1.06) |
| E46-10P | 12 | — | 2.16 (0.06) | — | 84.20 (2.30) | — |
| E40-10P | 12 | 13 | 2.22 (0.02) | 2.29 (0.02) | 92.75 (1.56) | 93.91 (1.68) |
| E46-15P | 17 | 12 | 2.20 (0.07) | 2.30 (0.03) | 90.21 (2.49) | 93.41 (2.25) |
| E40-15P | 13 | 9 | 2.26 (0.05) | 2.24 (0.03) | 94.37 (2.89) | 92.77 (2.30) |

Example 20—Fracture Toughness

The results obtained for the fracture toughness of the experimental formulations are shown in Table 12. The fracture toughness increased with increasing percentage of rubber-toughened polymer. These rubber particles actually absorbed energy prior to fracture, and, therefore decreased the probability that the crack attained the critical length for fracture. Rubber particles acted as a barrier to microcrack propagation by deforming more than the PMMA matrix, consequently absorbing more energy. The crack propagated mainly within the matrix surrounding the rubber beads. This explained the increase in fracture toughness for increased amounts of Esschem.

TABLE 12

Comparison of Fracture Toughness Results

| Bone Cement | Number of Specimens (n) 24 hours | Number of Specimens (n) 7 days | Fracture Toughness (Mpa · m$^{1/2}$) 24 hours | Fracture Toughness (Mpa · m$^{1/2}$) 7 days |
|---|---|---|---|---|
| S (prior art) | 14 | 4 | 1.94 (0.10) | 1.54 (0.29) |
| S5E | 6 | — | 2.21 (0.30) | — |
| S10E | 4 | — | 2.15 (0.20) | — |
| E46-0 (prior art) | 12 | 7 | 2.78 (0.45) | 2.51 (0.21) |
| E40-0 (prior art) | 13 | 7 | 2.48 (0.29) | 2.34 (0.21) |
| E46-5P | 7 | — | 2.51 (0.25) | — |
| E40-5P | 5 | — | 2.34 (0.15) | — |
| E46-15P | 6 | 7 | 2.28 (0.29) | 2.12 (0.09) |
| E40-15P | — | 6 | — | 2.05 (0.07) |

Analysis of the fracture surfaces of conventional bone cement (Simplex P) versus the rubber modified cement (Esschem) revealed that the fracture mechanism changed as the Esschem content increased. Simplex P showed flat propagation of the crack with a smooth fracture surface morphology. PMMA particles exhibited brittle fracture and appeared to be cleaved. The appearance of the fracture surface of the rubber-modified cement was more irregular, showing smooth and rough regions. In the smooth regions the crack propagated directly through the beads and matrix fracturing the particles. In the rough region the mechanism changed to ductile tearing.

Patents and publications mentioned in the specification are indicative of the levels of those skilled in the art to which the invention pertains. These patents and publications are incorporated herein by reference to the same extent as if each individual patent or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A bone cement formulation comprising:
a solid component pack comprising from 3 to 25 solid component pack weight percent of a polyacrylate and between 53.5 and 86.3 solid component pack weight percent of rubber toughened polymethyl methacrylate having a rubber toughener selected from the group consisting of: polyethylene, polypropylene, polybutene, polypentene, ethylene-propylene copolymers, isoprene-butene copolymers, ethylene-butene copolymers, polybutadiene, polyisoprene, hydrogenated polybutadiene, hydrogenated polyisoprene, ethylene-propylene-diene copolymers, ethylene-butene-diene copolymers, butyl rubber, polystyrene, styrene-butadiene copolymers, styrene-hydrogenated butadiene copolymers, and ligand forms thereof at 20° C.; and
a separately packaged liquid component pack comprising a polymerizable acrylate monomer.

2. The formulation of claim 1 wherein said polyacrylate is an acrylic acid ester of an aliphatic $C_1$-$C_2$ alcohol.

3. The formulation of claim 1 wherein said acrylate monomer is selected from a group consisting of: methyl methacrylate, ethyl methacrylate, isopropylmethacrylate, 2-hydroxyethyl methacrylate, n-butyl methacrylate, isobutyl methacrylate, 3-hydroxypropyl methacrylate, tetrahydrofurfuryl methacrylate, glycidyl methacrylate, 2-methoxyethyl methacrylate, 2-ethylhexyl methacrylate, benzyl methacrylate, 2,2-bis(methacryloxyphenyl)propane, 2,2-bis[4-(2-hydroxy-3-methacryloxypropoxy)phenyl]propane, 2,2-bis(4-methacryloxypolyethoxyphenyl)propane, ethylene glycol dimethacrylate, diethylene glycol dimethacrylate, triethylene glycol dimethacrylate, butylene glycol dimethacrylate, neopentyl glycol dimethacrylate, 1,3-butanediol dimethacrylate, 1,4-butanediol dimethacrylate, 1,6-hexanediol dimethacrylate, trimethylolpropane trimethacrylate, trimethylolethane trimethacrylate, pentaerythritol trimethacrylate, trimethylolmethane trimethacrylate and pentaerythritol tetramethacrylate.

4. The formulation of claim 1 wherein said polyacrylate is polymethyl methacrylate.

5. The formulation of claim 1 wherein said acrylate monomer is methyl methacrylate.

6. The formulation of claim 1 wherein said solid component pack further comprises a polymerization initiator.

7. The formulation of claim 1 wherein said liquid component pack further comprises a polymerization accelerant.

8. The formulation of claim 1 wherein said solid component pack further comprises a radiopaque agent.

9. The formulation of claim 1 wherein said liquid component pack further comprises a polymerization inhibitor.

10. A method of fixing a prosthetic implant to a patient's bone which comprises applying a bone cement formulation as claimed in claim 1 to a prosthesis attachment site.

* * * * *